United States Patent [19]

Anderson

[11] Patent Number: 5,629,159
[45] Date of Patent: May 13, 1997

[54] IMMORTALIZATION AND DISIMMORTALIZATION OF CELLS

[75] Inventor: David J. Anderson, Altadena, Calif.

[73] Assignee: California Institute of Technology, Pasadena, Calif.

[21] Appl. No.: 481,127

[22] Filed: Jun. 7, 1995

[51] Int. Cl.$^6$ ..................... C12Q 1/68
[52] U.S. Cl. ............. 435/6; 435/69.1; 435/172.3; 435/194; 435/325; 435/357; 435/363; 435/366; 435/372; 435/368
[58] Field of Search ............. 435/240.2, 172.3, 435/320.1, 6, 69.1, 194

[56] References Cited

U.S. PATENT DOCUMENTS

| | | | |
|---|---|---|---|
| 5,387,237 | 2/1995 | Fournier et al. | 623/11 |
| 5,399,346 | 3/1995 | Anderson et al. | 424/93.21 |

FOREIGN PATENT DOCUMENTS

| | | |
|---|---|---|
| 0220009 | 2/1993 | European Pat. Off. |
| 9215694 | 9/1992 | WIPO |
| 9322443 | 11/1993 | WIPO |
| 9402593 | 2/1994 | WIPO |

OTHER PUBLICATIONS

Orban, P.C., et. al., "Tissue–and Site–Specific DNA Recombination in Transgenic Mice." *Proc. Natl. Acad. Sci. USA*, 89:6861–6865 (1992).

Gossen, M., et al., "Tight Control of Gene Expression in Mammalian Cells by Tetracycline-Responsive Promoters." *Proc. Natl. Acad. Sci. USA*, 89:5547–5551 (1992).

O'Gorman, S., et al., "Recombinase–Mediated Gene Activation and Site-Specific Integration in Mammalian Cells." *Science*, 251:1351–1355 (1991).

Lakso, M., et al., "Targeted Oncogene Activation by Site–Specific Recombination in Transgenic Mice." *Proc. Natl. Acad. Sci., USA*, 89:6232–6236 (1992).

Hoess, R.H., et al., "Mechanism of Strand Cleavage and Exchange in the Cre–lox Site-specific Recombination System", *J. Mol. Biol.*, 181:351–362 (1985).

Abremski, K., et al., "Studies on the Properties of P1 Site–Specific Recombination: Evidence for Topologically Unlinked Products following Recombination", *Cell*, 32:1301–1311 (1983).

Sauer, B., et al., "Cre–stimulated recombination at loxP–containing DNA sequences placed into the mammalian genome", *Nucleic Acids Research*, 17(1):147–161 (1989).

Sauer, B., et al., "Site-specific DNA recombination in mammalina cells by the Cre–recombinase of bacteriophage P1", *Proc. Natl. Acad. Sci. USA*, 85:5166–5170 (1988).

Jayaram, M., et al., "Two–micrometer circle site–specific recombination: The minimal substrate and the possible role of flanking sequences", *Proc. Natl. Acad. Sci. USA*, 82:5875–5879 (1985).

Sternberg, N., et al., "Bacteriophage P1 Site–specific Recombination", *J. Mol. Biol.*, 150:467–486 (1981).

Gronostajski, R.M., et al., "Determination of DNA Sequences Essential for FLP mediated Recombination by a Novel Method", *The Journal of Biological Chemistry*, 260(22):12320–12327 (1985).

Senecoff, J.F., "The FLP recombinase of the yeast 2µm plasmid: Characterization of its recombination site", *Proc. Nat. Acad. Sci. USA*, 82:7270–7274 (1985).

*Primary Examiner*—James Ketter
*Attorney, Agent, or Firm*—Flehr Hohbach Test Albritton & Herbert; Richard F. Trecartin; Robin M. Silva

[57] ABSTRACT

Methods and compositions for the conditional immortalization of cells are provided.

39 Claims, 5 Drawing Sheets

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 12 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:1:

TGACTGACCT GA  12

IMMORTALIZATION AND DISIMMORTALIZATION OF CELLS

FIELD OF THE INVENTION

The invention relates to methods and compositions for the immortalization and disimmortalization of cells, and in particular to the methods as applied to gene therapy.

BACKGROUND

Gene therapy, whereby exogeneous nucleic acid is added to a cell to correct genetic defects or to treat disorders, is a rapidly emerging field. Frequently, gene therapy is done uses a patient's cells as the vehicle for the exogeneous nucleic acid; that is, cells may be excised from a patient, genetically manipulated, and reintroduced into the patient. See for example U.S. Pat. No. 5,399,346.

One problem with this approach is that excised cells generally have a finite lifespan in culture, absent further genetic manipulation. Thus, frequently, excised cell lines are transformed with an immortalization gene such as an oncogene. This allows indefinite growth and proliferation of the cells. However, immortalized cells containing oncogenes are unsuitable transplant candidates, due to the undesirability of introducing oncogenes into a patient.

Accordingly, it is an object of the invention to provide methods and compositions for the creation of immortalized cell lines which may be grown and perpetuated ex vivo, and then induced to disimmortalize, that is, remove the oncogenes, before introduction into a patient or animal.

SUMMARY OF THE INVENTION

In accordance with the forgoing object, the invention provides an isolated immortalized cell that contains recombinase target sites flanking an immortalization gene in the genome of the cell. The target sites are capable of mediating excision of the immortalization gene when the target sites are contacted with a recombinase.

In a further aspect, the immortalized cells comprise additional exogeneous nucleic acid comprising a selection marker gene, which may be a positive or negative selection marker gene. The cells may also contain a STOP site, and an additional selection marker gene.

In an additional aspect, methods are provided for creating an immortalized cell that contains recombinase target sites flanking an immortalization gene in the genome of said immortalized cell. The method comprises transforming a cell with exogeneous nucleic acid comprising a) a first recombinase target site; b) an immortalization gene; and c) a second recombinase target site, such that in the absence of a recombinase said exogeneous nucleic acid is incorporated into the genome of said cell. The exogeneous nucleic acid may also comprises at least one selection marker gene.

Further methods are provided for the disimmortalization of an immortalized cell that contains exogeneous nucleic acid comprising recombinase target sites flanking an immortalization gene in the genome of said immortalized cell. The method comprises contacting said recombinase target sites with a recombinase capable of recognizing said recombinase target sites.

An additional aspect of the invention provides methods for the disimmortalization of an immortalized cell. The method comprises incorporating exogeneous nucleic acid comprising a first recombinase target site; an immortalization gene; a negative selection marker gene; and a second recombinase target site. The exogeneous nucleic acid is incorporated into the genome of a cell to produce an immortalized cell which contains an excisable immortalization gene in an orientation such that excision of the sequence between the recombinase target sites excises the immortalization gene and the negative selection marker. The method further comprises contacting the recombinase target sites with a recombinase which recognizes said recombinase target sites such that said immortalization gene and said negative selection marker gene are excised. Cells which have not excised the immortalization gene and negative selection gene are selected against by culturing the cells in the presence of an appropriate negative selection agent.

Additional methods are provided for the disimmortalization of an immortalized cell. The method comprises incorporating exogeneous nucleic acid comprising a) a first recombinase target site; an immortalization gene; a selection marker gene; and a second recombinase target site. The nucleic acid is incorporated into the genome of a cell to produce an immortalized cell which contains an excisable immortalization gene in an orientation such that excision of the sequence between the recombinase target sites excises the immortalization gene, resulting in the expression of the selection marker. The method further provides contacting said recombinase target sites with a recombinase which recognizes said recombinase target sites such that said immortalization gene is excised. The cells are then cultured with a positive selection agent. The cells which do not express the selection marker are selected against.

BRIEF DESCRIPTION OF THE DRAWINGS

FIGS. 1A, 1B, 1C and 1D depict the design of four vectors for conditional immortalization. RTS is a recombinase target site. MPCS is a multiple polylinker cloning site, into which an immortalization gene is inserted. STOP is a translation or transcription stop sequence. LTR is a viral long terminal repeat. SV40 is the promoter from SV40.

FIG. 2(A) and 2(B) are two alternative designs for the same basic vector. In both vectors, the oncogene coding sequences (v-myc, BCl-2, or MASH-1) are inserted into a multiple polylinker cloning site (MPCS) flanked by RTSs, i.e. loxP sites. Downstream of the MPCS there is a "STOP" sequence designed to prevent translation of a downstream selectable marker (alkaline phosphatase, green fluorescent protein, lacZ, etc.). There is also a drug selection maker to select for initial immortalization of the cells. The drug-selection maker is driven by the viral LTR and the oncogene by an internal promoter-enhancer (2A) or vice-versa (2B).

FIG. 3A utilizes the immortalization gene as the selection marker for transformation; alternatively, clonal analysis using exposure to a negative selection agent can serve as the marker for transformation. FIG. 3B uses a positive selection marker as the marker for transformation. The positive and negative selection marker genes may be located in any order. FIG. 3C adds a recombinase under the control of an inducible promoter; a positive selection gene may also be added. Again, these genes may be located in any order. The promoters for transcription of genes other than the recombinase are not depicted, as they may be located at a variety of locations.

FIG. 4A allows the expression of the immortalization gene and first selection marker gene, with the second selection marker gene not expressed until excision between the two RTS1s. Upon RTS 1 excision, the second selection marker gene is expressed, allowing selection for disimmortalized cells. Prior to transplantation, exposure to the recombinase recognizing RTS 2 excises the second selection marker, thus minimizing the exogeneous nucleic acid. FIG. 4B is similar, except that an exogeneous gene is included, for example, encoding a therapeutic agent. Thus, cells may be transplanted with the exogeneous gene expressed, and at some later time the patient is exposed to the second recombinase to remove the exogeneous gene.

FIGS. 6A and 6B correspond to the construct depicted in FIG. 1C, but with a recombinase gene under the control of an inducible promoter. FIG. 6A depicts a construct which will leave the recombinase gene in the genome after excision, and FIG. 6B depicts a construct which eliminates the recombinase gene.

DETAILED DESCRIPTION OF THE INVENTION

The invention is directed to methods and compositions for the conditional immortalization of cells. By "conditional immortalization" herein is meant a process whereby cells are immortalized such that they can be disimmortalized at some later time. Thus, under certain conditions, the cells are immortalized; under different conditions, as outlined below, the cells are no longer immortalized, they return to their normal senescence pattern, and no longer grow and proliferate indefinitely in cell culture.

As is understood by those in the art, by "immortalized" herein is meant that the cells have been transformed with an immortalization gene, such that expression of the immortalization gene confers the ability to grow and proliferate substantially indefinitely in culture.

By "immortalization gene" herein is meant a gene which overcomes senescence mechanisms of a cell, allowing the cell to be subcultured substantially indefinitely. Immortalization genes are well known in the art. The immortalization gene is general is exogeneous to the cells used, and is generally integrated into the genome of the cell. Examples of immortalizing genes include: (1) nuclear oncogenes such as v-myc, N-myc, T antigen and Ewing's sarcoma oncogene (Fredericksen et al. (1988) Neuron. 1:439–448; Bartlett, P. et al. (1988) Proc. Natl. Acad. Sci. USA 85:3255–3259, and Snyder, E. Y. et al. (1992) Cell 68:33–51), (2) cytoplasmic oncogenes such a E. et al. (1991) Science 254:1153–1160), (3) membrane oncogenes such as neu and ret (Aaronson, A. S. A (1991) Science 254:1153-116 1), (4) tumor suppressor genes such as mutant p53 and mutant Rb (retinoblastoma) (Weinberg, R. A. (1991) Science 254:1138–1146), and (5) other immortalizing genes such as Notch dominant negative (Coffman, C. R. et al. (1993) Cell 23:659–671). Particularly preferred oncogenes include v-myc and the SV40 T antigen.

By "disimmortalization" herein is meant a process whereby all or part of the immortalization gene of an immortalized cell is physically excised from the genome of the cell, allowing the cell to return to a more normal senescence cycle, such that it no longer grows and proliferates indefinitely in culture. A disimmortalized cell may have all or part of the conditional immortalization construct removed. Thus, as will be appreciated by those in the art, in conjunction with the disclosure herein, a variety of conditional immortalization constructs may be made, resulting in different mounts of exogeneous nucleic acid left in the cell genome. In a preferred embodiment, all of the immortalization gene is removed from a disimmortalized cell.

The methods of conditional immortalization and disimmortalization of the invention are accomplished using a site-specific recombinase system. Several such systems are known, including the Cre recombinase from the bacteriophage P1, and the FLP ("flip") recombinase from Saccharomyces cerevisiae. The Cre system utilizes the Cre recombinase, which is a 38 kDa protein, and two 34 basepair recombinase target sites (RTS), termed loxP. Recombination can occur between directly repeated loxP sites on the same molecule to excise the intervening DNA segment. See Sauer et al., Proc. Natl. Acad. Sci. USA 85:5166 (1988); Sauer et al., Nuc. Acids Res. 17:147 (1989); Lakso et al., Proc. Natl. Acad. Sci. USA 89:6232; Hoess et al., J. Mol. Biol. 181:351–362 (1985); Abremski et al., Cell 32:1301 (1983); Sternberg et al., J. Mol. Biol. 150:467–486 (1981); and Orban et al., Proc. Natl. Acad. Sci. USA 89:6861 (1992). The FLP system utilizes the FLP protein and two FLP recombination target sites (termed FRT in the art; depicted herein as RTSs) that consist of two 13 inverted basepair repeats and an 8 basepair spacer (See for example O'Gorman, Science 251:1351 (1991); Jayaram, PNAS USA 82:5875–5879 (1985); Senecof et al., PNAS USA 82:7270 (1985); and Gronostajski et al., J. Biol. Chem. 260:12320 (1985)). All of these references are expressly incorporated by reference.

By "recombinase target site" (RTS) herein is meant a nucleic acid sequence which is recognized by a recombinase for the excision of the intervening sequence. It is to be understood that two RTSs are required for excision. Thus, when the cre recombinase is used, each RTS comprises a loxP site; when loxP sites are used, the corresponding recombinase is the cre recombinase. That is, the recombinase must correspond to or recognize the RTSs. When the FLP recombinase is used, each RTS comprises a FLP recombination target site (FRT); when FRT sites are used, the corresponding recombinase is the FLP recombinase.

Using these recombinase systems, the immortalization genes inserted into a host cell may be excised upon exposure to the appropriate recombinase. Thus, the conditional immortalization constructs are inserted into a cell in an orientation that results in the expression of the immortalization gene. For all of the embodiments, the host cells must not contain nucleic acid encoding the appropriate recombinase prior to the addition of the exogeneous nucleic acid of the invention. At some later time, the recombinase is expressed and contacts the recombinase target sites to excise the intervening immortalization gene.

Preferably, selection marker genes are used to detect or select for successful immortalization and disimmortalization. For example, the expression of a first selection marker allows the detection of successful immortalization; that is, the marker gene is expressed when the immortalization gene has been integrated into the cell genome. The expression of a second selection marker, preferably different from the first selection marker gene, indicates the excision of the immortalization gene, as is more fully described below. These selection markers can be either positive or negative selection markers. As is known in the art, "selection marker gene" or equivalents means genes that allow the selection of cells containing the gene. "Positive selection" refers to a process whereby only cells that contain the positive selection marker will survive upon exposure to the positive selection agent or be marked. For example, drug resistance is a common positive selection marker; cells containing the drug resistance gene will grow on medium containing the drug, and those cells which do not contain the resistance gene will die. Suitable drug resistance genes are histidinol dehydrogenase, neomycin-resistance, hygromycine-resistance, and puromycin-resistance, among others. Other positive selection marker genes include genes that allow the sorting or screening of cells. These genes include the alkaline phosphatase gene, the gene for green fluorescent protein, the lacZ gene, and surface markers such as CD8, among others. In one embodiment, as is described below, the immortalization gene may serve as a positive selection marker.

Of particular use in this invention are negative selection markers, the use of which is outlined below. "Negative selection" refers to a process whereby cells transfected with a negative selection marker are killed upon exposure to an appropriate negative selection agent which kills cells containing the negative selection marker. For example, cells which contain the herpes simplex virus-thymidine kinase (HSV-tk) gene are sensitive to gancyclovir (GANC$^S$). Similarly, the Gpt gene renders cells sensitive to 6-thioxanthine. When appropriately positioned in a conditional immortalization construct, the negative selection marker gene can be used to isolate cells which have been disimmortalized. That is, the negative selection marker is expressed with the immortalization gene, such that if the immortalization gene is still present, the cells will be killed.

Generally, the conditional immortalization-disimmortalization vectors and technique proceeds as follows. The gene constructions used for immortalization are set up in such a way that a first transformation with exogeneous nucleic acid results in immortalization. The cells may be grown and propagated and other genes may be added, as outlined above. In some instances, when the cells are stem cells, the immortalized cells may be differentiated if desired. Then prior to transplantation or at some later time, the cells are manipulated such that the immortalization gene is excised; i.e. the cells are disimmortalized.

In a preferred embodiment, the cloning vector which introduces the immortalization gene into the cells is constructed such that the immortalization gene, any selection markers, promoters and RTSs are integrated into the genome simultaneously. That is, further integration of DNA into the genome is not needed to facilitate disimmortalization. Alternatively, the immortalization gene may be introduced into the genome with sufficient flanking sequences to allow the construction of homologous recombination vectors to introduce the additional required sequences.

In a preferred embodiment, disimmortalization occurs as a result of a further transformation with exogeneous nucleic acid encoding the recombinase, as is outlined below.

In one embodiment, the invention provides conditionally immortalized cell lines. These immortalized cell lines contain nucleic acid which comprises a variety of different conditional immortalization constructs as outlined below.

These immortalized cell lines may be made by transforming at least one cell with nucleic acid comprising the contructs of the invention.

These conditionally immortalized cell lines may be used in a variety of methods for disimmortalization, as outlined below.

In another embodiment, the cell lines contain nucleic acid comprising recombinase target sites that flank an immortalization gene in the genome of the cells of the cell lines. These target sites must be in an orientation such that the RTSs are capable of mediating excision of the immortalization gene when the RTSs are contacted with a recombinase. That is, in the absence of the recombinase which recognizes the RTSs, the immortalization gene is incorporated into the genome of the cell and expressed, to create an immortalized cell line. When the RTSs are exposed to the corresponding recombinase, excision of the sequence between the RTSs occurs. Since this sequence contains the immortalization gene, the excision event results in a loss of the gene, i.e. disimmortalization.

Figures 3A, 3B:
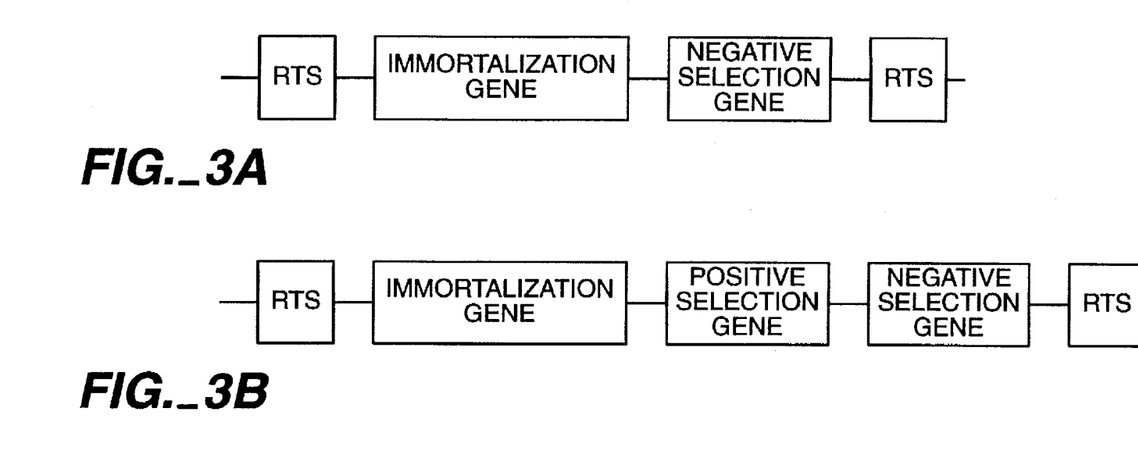
FIGS. 3A, 3B and 3C depict immortalization/disimmortalization constructs using negative selection markers to insure that all cells have been disimmortalized.

In a further embodiment, the invention provides immortalized cell lines that contain nucleic acid comprising a first recombinase target site, an immortalization gene, a negative selection marker gene, and a second recombinase target site, as is generally depicted in FIG. 3A. As above, in the absence of the recombinase which recognizes the RTSs, the immortalization gene is incorporated into the genome of the cell and expressed, to create an immortalized cell line. The RTSs are capable of mediating excision of the immortalization gene when the RTSs are contacted with a recombinase. In a preferred embodiment, the immortalization and negative selection marker genes are flanked by the RTSs. Thus, upon transformation, the immortalization gene and negative selection marker are expressed, and transformed cells may be selected on the basis of immortalization or expression of the negative selection marker. Upon exposure to or contact with a recombinase that recognizes the RTSs, the immortalization gene and negative selection marker are excised, and disimmortalized cells may be selected by exposure to the negative selection agent. That is, disimmortalized cells will survive, and those that still contain the immortalization gene and the negative selection marker gene will die.

Figure 4A:
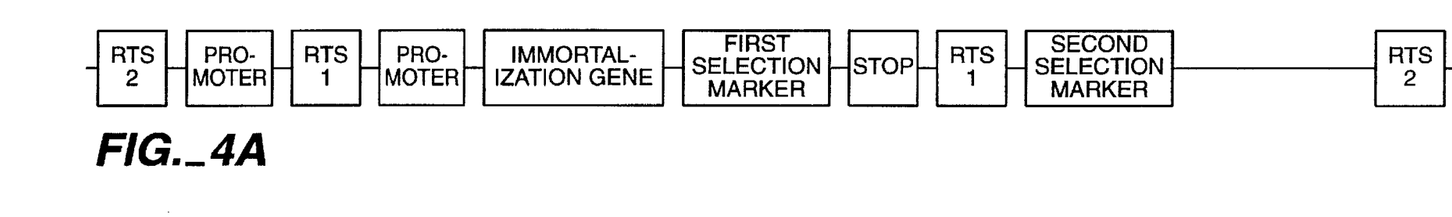
FIGS. 4A and 4B depict the use of two different recombinases and RTSs.
Figure 4B:
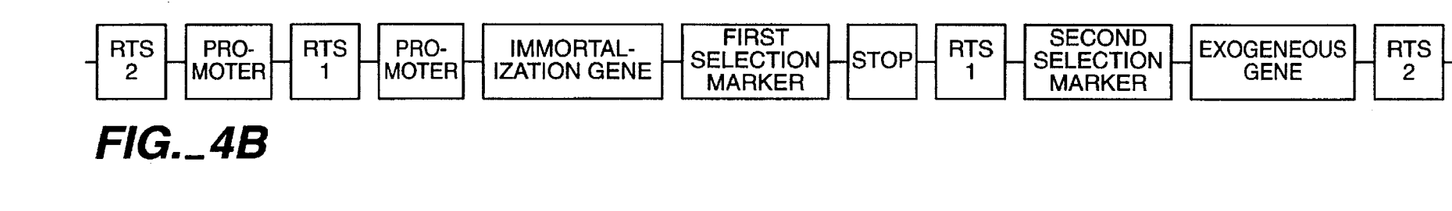
Figure 5:
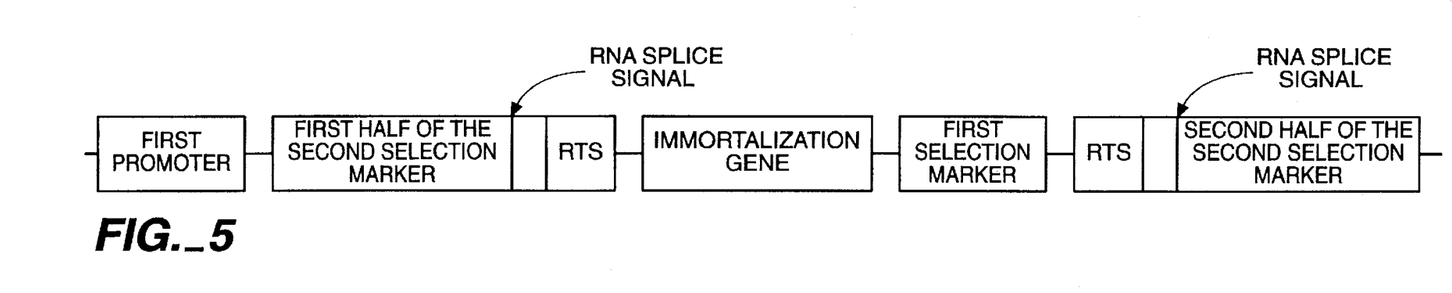
FIG. 5 depicts a conditional immortalization construct which avoids the use of a STOP site by putting the RTSs in the middle of a selection marker gene. Upon transformation of cells with this construct, the immortalization gene and first selection marker gene are transcribed, using a second promoter. Immortalized cells are then selected for on the basis of the first selection marker. Upon exposure to a recombinase that recognizes the RTSs, the immortalization gene and first selection marker are excised, along with the one of the RTS sites The second selection marker is transcribed, with the second RTS being removed as a result of RNA splice signals which are recognized by the cellular machinery of the host cells. This allows the second selection marker gene to be transcribed.

In an additional embodiment, the invention provides immortalized cell lines that contain nucleic acid comprising a first recombinase target site, an immortalization gene, a selection marker gene, and a second recombinase target site. As above, in the absence of the recombinase which recognizes the RTSs, the immortalization gene is incorporated into the genome of the cell and expressed, to create an immortalized cell line. The RTSs are capable of mediating excision of the immortalization gene when the RTSs are contacted with a recombinase. In one embodiment, the orientation of the construct is preferably such that in the absence of a recombinase, the immortalization gene is expressed but the selection marker gene is not. This is preferably done through the addition of a STOP site to the construct, such as is shown in FIGS. 1 and 4, although as depicted in FIG. 5, it may also be accomplished by having one of the RTSs in the middle of the selection marker gene. Upon exposure to a recombinase which recognizes the RTSs, the intervening sequence is excised, resulting in a loss of the immortalization gene and the expression of the selection marker gene, thus allowing for selection of disimmortalized cells. Alternatively, the orientation of the construct is such that upon transformation, the immortalization gene and the selection gene are expressed, thus allowing selection for immortalization. Upon exposure to a recombinase that recognizes the RTSs, the immortalization gene and selection gene are excised, and the resulting cells may be selected for disimmortalization by a loss of the selection gene.

In a further embodiment, the invention provides immortalized cell lines containing nucleic acid comprising a first recombinase target site, an immortalization gene, a first selection marker gene, a second recombinase target site, and a second selection marker gene. In this embodiment, the orientation of the construct is such that upon transformation, the immortalization gene and the first selection marker gene are expressed, and the second selection marker gene is not. This is preferably accomplished by the addition of a STOP site to the construct, although as above it may be done in alternative ways. Upon exposure or contact with a recombinase that recognizes the RTSs, the immortalization gene and the first selection marker gene are excised, and the second selection marker is expressed. This allows for selection of disimmortalized cells on the basis of the second selection marker gene.

Several specific embodiments are shown in the Figures, which utilize a preferred retroviral cloning vector with either the Cre/loxP or the FLP/FRT recombinase systems. Those skilled in the art will recognize that a variety of constructions will result in the creation of immortalized cells which can be subsequently disimmortalized, only several of which are shown in the Figures.

Figure 1A:
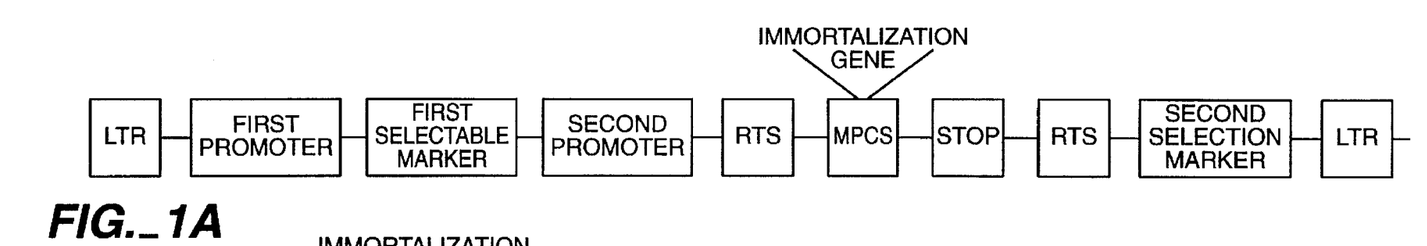
Figure 1B:
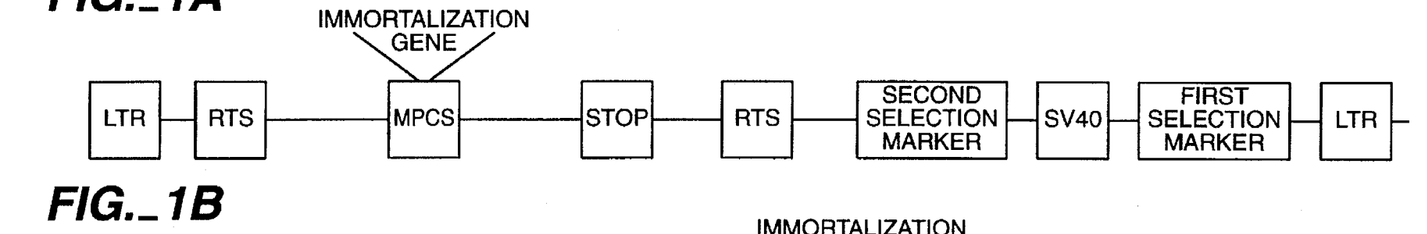
Figure 1C:
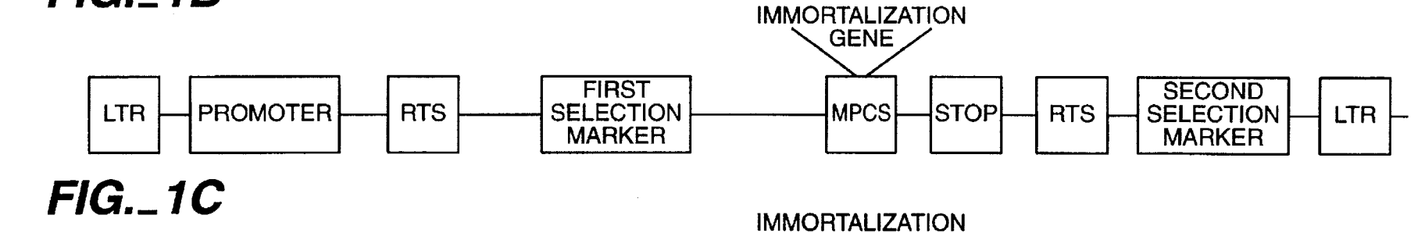
Figure 1D:
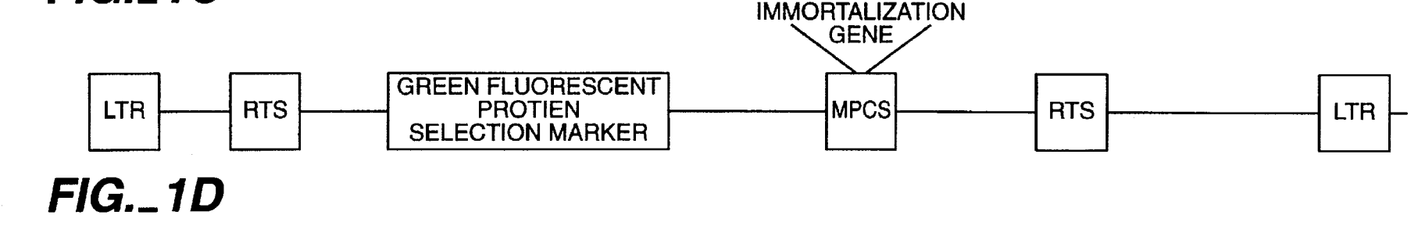
Figure 2A:
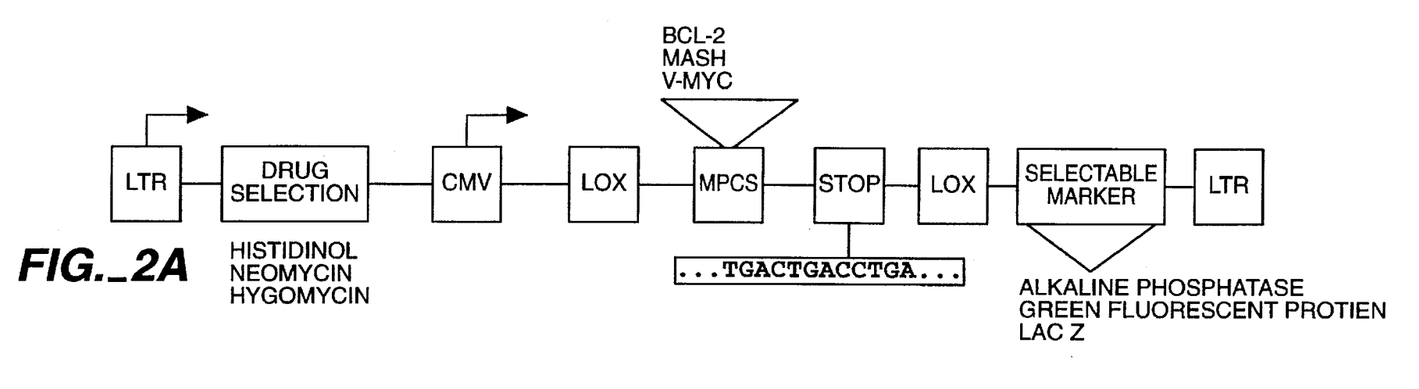
FIGS. 2A and 2B depict preferred embodiments.
Figure 2B:
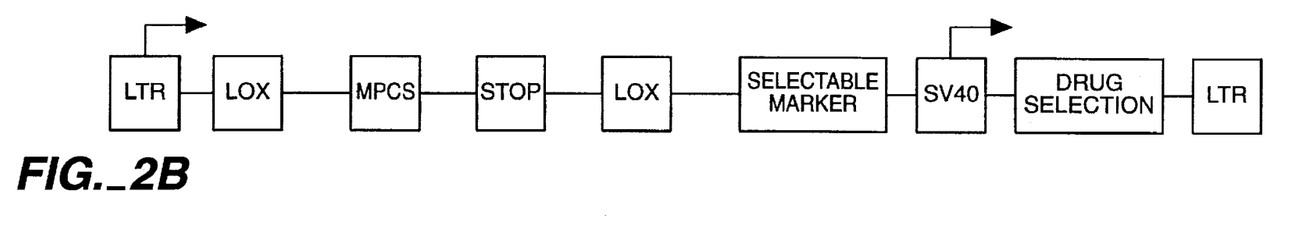

In a preferred embodiment, the conditional immortalization constructs are as depicted in FIGS. 1 and 2. First, a cloning vector is constructed which contains: a first selectable marker with a first promoter; a second promoter; a multiple polylinker cloning site (MPCS), flanked by the recombinase target sites (RTS); and a second selectable marker. The immortalizing gene, generally an oncogene, is inserted in the MPCS, along with a STOP sequence that prevents the expression of the second selectable marker. STOP sequences such as TGACTGACCTGA (SEQ ID NO:1) are known in the art. Thus, in the absence of a recombinase, the immortalizing gene is expressed using the second promoter and the first selectable marker is expressed using the first promoter. This allows the selection of transformed, immortalized cells, but the STOP sequence prevents the expression of the second marker. Thus the immortalized cells may be cloned and grown, and additional genes added if desired. For disimmortalization, expression (preferably transient) of the appropriate recombinase, using techniques well known in the art, is accomplished. This results in the excision of the recombinase target sites, the MPCS containing the immortalization gene, and the STOP sequence. Thus, the second selectable marker gene is now expressed, and disimmortalized cells may be selected on the basis of this marker gene.

In FIG. 1A, the first selectable marker is translated via the first promoter (or alternatively, from a promoter internal to the LTR), and the immortalization gene inserted in the MPCS is driven by the second promoter. In the absence of a recombinase, the STOP sequence prevents the translation of the second selectable marker. Upon exposure to the recombinase, the immortalization gene and the STOP sequence are excised, allowing the second selectable marker to run off the second promoter. In FIG. 1B, translation of the immortalization gene is driven by the internal LTR promoter, the first selectable marker is translated via the SV40 promoter or equivalents, but the STOP sequence prevents the translation of the second selectable marker. Upon exposure to the recombinase, the immortalization gene and the STOP sequence are excised, allowing the translation of the second selectable marker. In FIG. 1C, the first selectable marker and the immortalization gene are translated via either a first promoter or the LTR promoter, but the STOP sequence prevents the translation of the second selectable marker. Upon exposure to the recombinase, the immortalization gene and the STOP sequence are excised, allowing the translation of the second selectable marker via the promoter or the LTR. In FIG. 1D, translation of the green fluorescence protein and the immortalization gene occur via the LTR promoter (or another promoter). The green fluorescent protein serves as a selection marker. Upon exposure to the recombinase, the immortalization gene and the green fluorescent protein coding sequence are excised. Thus, the cells may be selected first by the presence of the green fluorescent protein and then by its absence.

The RTSs are exposed to or contacted with a recombinase in any number of ways. By "exposed to" or "contacted with a recombinase that recognizes the RTSs" herein is meant that the recombinase protein must interact with the RTSs in a manner which allows the excision of the sequence between the RTSs. Generally, all that is required is that the recombinase be present within the cell containing the RTSs. This may be done by expressing the recombinase in the cells containing the conditional immortalization construct, as outlined below.

In a preferred embodiment, the expression of the recombinase is transient, since generally the site specific recombination is rapid and efficient. Transient expression is achieved by a variety of methods well known in the art, including, but not limited to, transfection of plasmid DNA by calcium phosphate precipitation, electroporation, lipofection or other physical-chemical methods, transduction using a retroviral vector, or expression from another recombinant viral vector such as an adenovirus. Adenoviral expression is particularly preferred since high expression efficiencies are common.

Figure 3C:
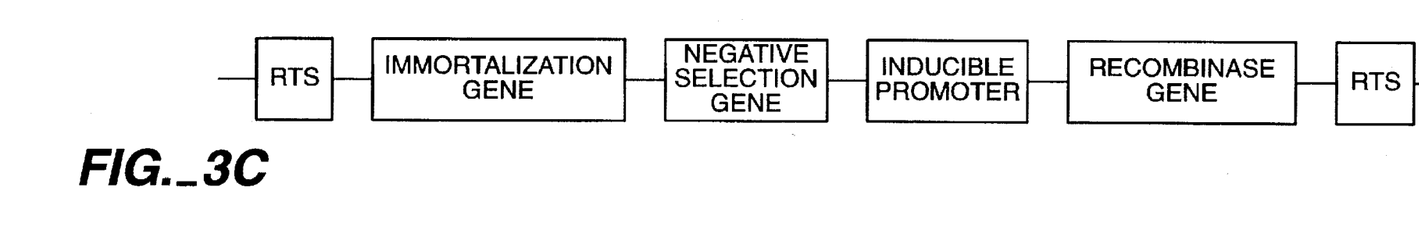
Figure 6A:
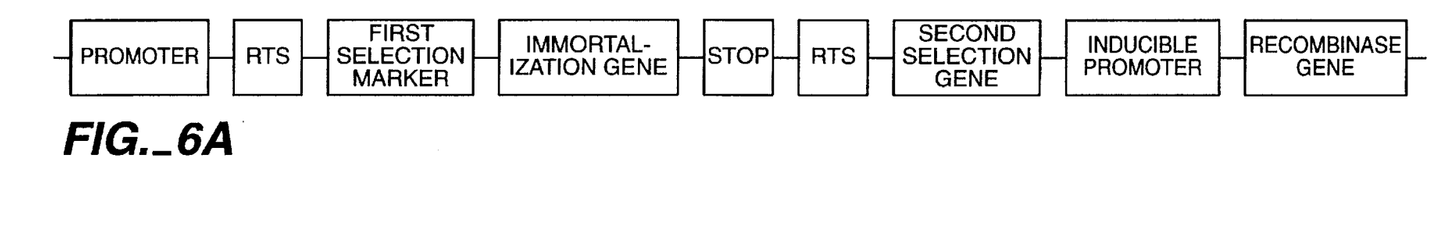
FIGS. 6A and 6B depict the use of an inducible promoter with the recombinase gene.
Figure 6B:
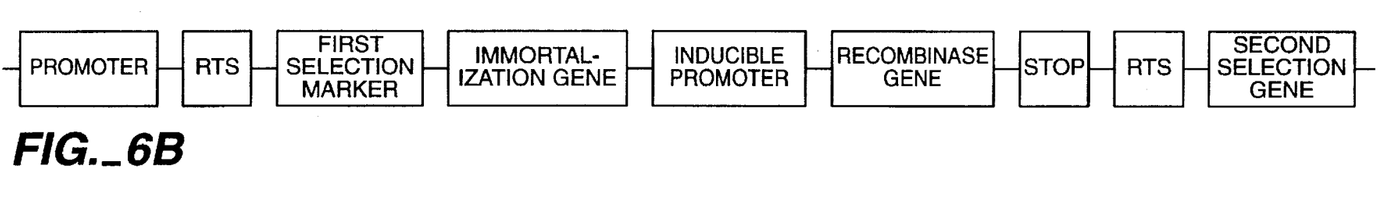

In an alternate embodiment, the gene encoding the recombinase is placed under the control of an inducible promoter and is part of the immortalization/ 5 disimmortalization construct. Generally, an inducible promoter operably linked to the recombinase gene may be included in any of the embodiments depicted in the Figures. Constructs of this type are generally depicted in FIGS. 6 and 3C. FIG. 6A corresponds to FIG. 1c with an inducible promoter/recombinase gene added, which will be left in the genome. FIG. 6B corresponds to FIG. 1C when the recombinase will be excised. Since only a small amount of recombinase is necessary to result in the excision of the sequences between the RTSs, it is desirable to use tightly regulated promoters to avoid premature recombination events. Transcription stop signals flanking the recombinase are also desirable. Recombination and excision of the immortalization gene, and preferably the recombinase gene, occurs as when the appropriate inducing conditions are administered.

In a preferred embodiment, negative selection markers are used, or a combination of positive and negative selection markers. Negative selection markers are particularly useful to prevent immortalized cells from being transplanted. For example, negative selection markers may be expressed with the immortalization gene. After disimmortalization, the cells are exposed to the negative selection agent, such as GANC, which kills any cells which still contain the HSV-tk gene that is closely linked to immortalization gene. Particular examples are shown in FIG. 3. In FIG. 3A, the RTSs flank an immortalization gene and a negative selection gene. As described above, the immortalization gene serves as the first selection marker. Alternatively, clonal colonies which contain the negative selection gene may be identified by using the negative selection marker; that is, clonal colonies are used to identify parent colonies which contain the negative selection gene. The promoter(s) used to drive the expression of the immortalization and negative selection genes may be located on either side of the first RTS. When contacted with a recombinase, the immortalization gene and negative selection gene are excised, and the cell is disimmortalized. Any remaining immortalized cells may be killed by exposing the putatively disimmortalized cells to the negative selection agent; in the case of the herpes simplex virus thymidine kinase gene, for example, the cells may be exposed to GANC. This reduces and potentially eliminates remaining immortalized cells, which is desirable when the cells are transplantation. This construct is particularly preferred since it results in very little if any exogenous nucleic acid remaining in the genome of the cell, which is also desirable for transplantation. In FIG. 3B, there is a positive selection gene included in the construct to select for immortalized cells. In FIG. 3C, the system is similar to FIG. 3A except that the recombinase under the control of an inducible promoter is included, eliminating the need for further genetic manipulation.

In a preferred embodiment, STOP sites are used to prevent translation of selection markers prior to disimmortalization, as is generally outlined above for a variety of constructs. Alternatively, as depicted in FIG. 5, it is possible to prevent expression of functional selection markers by putting the RTSs in the middle of selection marker genes. This method relies on the faithful excision of the RTSs by the recombinase, since any remaining nucleotides will most likely result in frameshift mutations and thus a non-functional selection marker.

In an additional embodiment, more than one set of RTSs are used. This may be done using additional sets of RTSs which are recognized by the same recombinase, or alternatively, by using RTSs which are recognized by a different recombinase.

When additional sets of RTSs for the same recombinase are used, care should be taken in designing the constructions such that excision between any two RTSs gives a desired or measurable result. That is, since excision can occur between any two RTSs, it is possible that a single RTS, with flanking exogenous nucleic acid will be left within the genome.

In a preferred embodiment, sets of RTSs from different recombinases are used. This may be of particular use when additional exogenous genes are included in the genome. For example, using the construct depicted in FIG. 4A, immortalized cells are selected using the first selection marker. For disimmortalization, the recombinase which recognizes the RTS 1 sites is used, and the disimmortalized cells selected using the second selection marker. The exogeneous gene may be transcribed using the first promoter, in which case it will be turned on only upon disimmortalization, or its own promoter, which allows transcription during the immortalized and disimmortalized states. The disimmortalized cells which express the exogeneous protein are transplanted. At some later time, for example when the exogeneous gene product is no longer required, exposure to the second recombinase results in excision of the second selection marker and the exogeneous gene. Alternatively, the exogeneous gene may only be required ex vivo, in which case the second recombinase may be used prior to transplantation. As for the other constructs described herein, those skilled in the art will be able to construct a variety of functionally similar constructs using the teachings herein.

In an additional embodiment, two recombinases are used to eliminate any exogenous nucleic acid prior to transplantation. For example, using the construct shown in FIG. 4B, immortalized cells are selected using the first selection marker. For disimmortalization, the recombinase which corresponds to the RTS 1 sites is contacted with the construct, and the cells selected on the basis of the second selection marker which is transcribed from the first promoter. The cells can then be contacted with a second recombinase which recognizes the RTS 2 sites prior to transplantation, to eliminate any exogenous nucleic acid. Although the excision event is very efficient, a loss of the selection marker using clonal colonies may be used for selection.

In one embodiment, the recombination event excises the first selectable marker. This may be preferred in situations where the disimmortalized cells are to be transplanted, and the it is desirable to minimize the introduction of exogenous genes into a patient.

In a preferred embodiment, the first selectable marker is a drug resistance gene such as histidinol dehydrogenase, neomycin-resistance, hygromycin-resistance, and puromycin-resistance, among others. In this embodiment, the second selectable marker is a gene that will allow the sorting or screening of cells, and can include the alkaline phosphatase gene, the gene for green fluorescent protein, the lacZ gene, surface markers such as CD8, or any of the genes outlined for the first selectable marker, as long as the first and second selectable markers are different genes within any single cell. In some embodiments, the transformation frequency may be so high that either the first or the second selectable markers may be eliminated, although generally it is preferable to retain at least the second selectable marker if the disimmortalized cells are destined for transplantation, since it is desirable to ensure that no cells containing oncogenes are transplanted into an animal. In one embodiment, a single selection marker is used, for example a marker such as the green fluorescent protein which allows for cell sorting. In this embodiment, the marker is expressed when the immortalizing gene is introduced, and the transformed cells are separated from the non-transformed cells by cell sorting. Upon disimmortalization, the marker gene is eliminated, and the cells are resorted, with the disimmortalized cells lacking the marker.

In a further embodiment, the immortalized cells are selected on the basis of phenotype. For example, the immortalization gene may serve as the first selectable marker, since cells which do not contain the gene will not grow indefinitely in culture and may be eliminated on this basis. Alternatively, markers may be detected using clonal analysis; for example, when the HSV-TK gene is used, clones may be analyzed for TK activity.

As used herein, the term "genetically-engineered cell" or "recombinant cell" refers to a cell into which foreign (i.e., non-naturally occurring) nucleic acid, e.g., DNA, has been introduced. By "foreign" or "heterologous" or "exogenous" nucleic acid herein is meant nucleic acid which is not normally found within the genome of the cell, or is in a form not normally found within the genome. Thus, immortalization genes such as oncogenes or recombinase target sites may not be normally found in the genome of the host cell, and thus immortalized cells containing these sequences are genetically engineered. In some embodiments, the conditionally immortalized cells are manipulated to express one or more additional exogenous genes. Such genes may be normally contained within the genome, i.e. homologous, but not expressed to an appreciable extent, or are heterologous, i.e. not normally found within the genome. For example, homologous growth factor genes may be introduced to a cell in a form not normally found within the genome; i.e. with regulatory sequences such as promoters which allow expression of the growth factor at levels not normally seen in the cell, or within cell types that do not normally express the growth factor. Alternatively, heterologous genes can be introduced. Thus, the conditionally immortalized cells of the invention may be genetically engineered to contain more than one exogenous nucleic acid sequence.

The conditional immortalization constructs and method of the invention may also contain additional exogeneous genes. For example, genes encoding growth factors may be introduced to facilitate the survival of transplanted cells, or for the treatment of the patient. For example, neurotrophins including nerve growth factor (NGF), neurotrophin-3 (NT3), neurotrophin-4 (NT4), and brain-derived neurotrophin factor (BDNF) may be useful. In the case where cells other than neural cells are used, appropriate exogenous genes include those encoding growth factors, such as human growth factor, epidermal growth factor, neural growth factors, etc.; cytokines; enzymes and enzyme inhibitors; interferons, such as $\alpha$, $\beta$ or $\gamma$-interferons; and other proteins.

Thus for example, cells may be immortalized for ex vivo manipulations such as the introduction of foreign DNA encoding therapeutic agents, and then disimmortalized, allowing the introduction into a patient of genetically engineered cells which express a therapeutic agent.

In one embodiment, the cells are removed from a patient with a genetic defect and engineered to contain at least one copy of a corrected gene before reintroduction of the cells using the techniques of the invention. Genetic disorders which may be treated in this manner are known in the art.

In addition to the immortalization gene, the cells of the invention have additional exogenous nucleic acid, as is more fully described below. This exogenous nucleic acid includes at least two recombinase target sites, and preferably selection and/or marker genes, transcription termination sites, linker sequences, and other genes of interest as described above.

The foreign nucleic acid or exogenous nucleic acid may be introduced by a variety of techniques known in the art, including, but not limited to, calcium-phosphate-mediated transfection, DEAE-mediated transfection, microinjection retroviral transformation, protoplast fusion and lipofection.

In a preferred embodiment, foreign DNA is introduced into cells using the technique of retroviral transfection. Recombinant retroviruses are used to introduce immortalization genes, selection or marker genes, recombinase target sites, and recombinases. The recombinant retroviruses are produced in packaging cell lines to produce culture supernatants having a high titer of virus particles (generally $10^5$ to $10^6$ pfu/ml). The recombinant viral particles are used to infect cultures of the cells or their progeny by incubating the cell cultures with medium containing the viral particles as is known in the art. Following retroviral infection, the cells are rinsed and cultured in standard medium. The infected cells are then analyzed for the uptake and expression of the foreign DNA. The cells may be subjected to selective conditions which select for cells that have taken up and expressed a selectable marker gene.

In a preferred embodiment, the cloning vector is a retroviral vector, and utilize long terminal repeats (LTR) as shown in the figures. Alternative embodiments utilize traditional expression plasmids, herpes virus-based vectors and adenovirus-based vectors, as well as other equivalents well known to those skilled in the art.

In another embodiment, the foreign DNA is introduced using the technique of calcium-phosphate-mediated transfection as is known in the art. For example, a calcium-phosphate precipitate containing the conditional immortalization constructs of the invention is prepared using the technique of Wigler et al. (1979) Proc. Natl. Acad. Sci. USA 76:1373–1376. Cultures of the cells are established in tissue culture dishes. Twenty four hours after plating the cells, the calcium phosphate precipitate containing approximately 20 pg/ml of the foreign DNA is added. The cells are incubated at room temperature for 20 minutes. Tissue culture medium containing 30 µM chloroquine is added and the cells are incubated overnight at 37° C. Following transfection, the cells are analyzed for the uptake and expression of the foreign DNA. The cells may be subjected to selection conditions which select for cells that have taken up and expressed a selectable marker gene.

The above techniques may be performed more than once on a particular cell; for example, these techniques may be used to introduce the immortalization gene with recombinase sites, and then to introduce further exogenous nucleic acid to the immortalized cells, such as any expression plasmid encoding a recombinase.

As will be appreciated by those in the art, a wide variety of suitable promoters may be used in the invention. Particularly useful promoters include, but are not limited to, the internal promoter enhancer of the LTR of retroviruses, the SV40 promoter, and tissue- or cell-type specific promoters, especially promoters specific for the cell type which is to be conditionally immortalized.

Suitable cells which can be used to practice the conditional immortalization methods of the invention include any cell type which does not produce a recombinase which recognizes the recombinase target sequence used in the constructs of the invention. Preferably, the cells are dividing such that they are capable of being infected by a retroviral vector. Suitable cells are vertebrate cells, preferably mammalian cells such as primate, ovine, porcine, bovine, canine, feline and equine for example, and more preferably human cells. Particularly preferred cells all types of stem cells such as neural, and hemopoietic cells. Suitable non-stem cells include islet cells, fibroblasts, osteoclasts, osteoblasts, epidermal and dermal cells, and endothelial cells.

In a preferred embodiment, the phenotype, growth, and life span of a disimmortalized cell is identical to the same cell type in the absence of any genetic manipulation; that is, a disimmortalized cell is identical to the starting cells, prior to immortalization. In alternative embodiments, the cells may have altered characteristics.

It should be recognized that in some cases, the starting cells are immortal in vivo; that is, they may exist indefinitely in the host animal, but are unable to grow indefinitely ex vivo. Thus, for example, islet cells appear to be "immortal", i.e. last a lifetime, in humans. Yet islet cells may still require immortalization for ex vivo growth and proliferation in cell culture. Similarly, stem cells such as neural stem cells may be immortal in vivo, or last for an extended period of time, and are capable of several cell cycles in vitro, but must be immortalized with an immortalization gene for indefinite growth and proliferation in cell culture.

It is to be understood that unless subjected to new culture conditions, cell division of an immortalized cell results in two substantially identical daughter cells; that is, immortalized cells are capable of indefinite regeneration. Thus, for example, cell division of immortalized stem cells such as neural crest stem cells results in two neural crest stem cells, both equally undifferentiated. Upon exposure to certain experimental or physiological conditions, these stem cells will undergo partial or complete differentiation.

As is understood by those skilled in the art, the culture conditions suitable for the immortalized cell lines will vary depending on the cell type.

The conditional immortalization methods of the invention find use in a number of applications, as will be appreciated by those skilled in the art.

In one embodiment, the conditionally immortalized cells are stem cells, and in a preferred embodiment the cells are neural crest stem cells and multipotent neural stem cells as are described in WO 94/02593, expressly incorporated herein by reference. As will be appreciated by those skilled in the art, neural stem cells, which lead to the formation of glia and neurons of the central and peripheral nervous system, can be transplanted or implanted to form new neurons and glia. For example, the replacement of motor neurons and their associated glial cells in the spinal cord for acute traumatic motor injury or the replacement of dying dopaminergic neurons in the midbrain for the treatment of Parkinson's Disease are both active areas which are being pursued in pre-clinical studies. A second application of the transplantation of genetically immortalized cells is for gene therapy; the cells can be genetically modified prior to transplantation so as to express a missing gene product and then the transplantation of these cells into the particular region of the brain will deliver the product of the gene in the area of the body where it is needed. Proof of principle for such gene therapy approaches has already been demonstrated in animal models using hereditary mucopolysaccharidosis as a test system.

In an alternate embodiment, cells other than stem cells may be immortalized for ex vivo growth and then disimmortalized prior to reintroduction into the body. For example, U.S. Pat. No. 5,387,237 describes a bioartificial pancreas comprising a plastic cylinder filled with porcine pancreatic islet cells. These porcine islet cells may be immortalized for ex vivo growth and proliferation, allowing uniformity over time, and then disimmortalized prior to introduction into the body. Those skilled in the art will realize that any variety of such systems could utilize the present invention.

For example, these methods can be used in any ex vivo gene therapy techniques, such as are generally described in U.S. Patent No. 5,299,346. Thus, any cells to be transplanted into a patient, whether human or animal, may be subjected to the conditional immortalization methods, with subsequent disimmortalization prior to transplantation. In one embodiment, the cells are removed from the patient into which they will be transplanted; in other embodiments, the cells are from other patients or other animals. For example, pig islet cells may be conditionally immortalized and disimmortalized prior to transplantation in a human, as is described in U.S. Pat. No. 5,387,237.

Thus, methods for introducing or transplanting disimmortalized cells such as stem cells into a host animal or mammal am provided. Transplantation techniques are well known in the art, and may be done with disimmortalized cells. Thus, for example, the disimmortalized cells may be transplanted into a host to evaluate the therapeutic potential of the cells, or to treat a neurological disorder of the nervous system. In a preferred embodiment, the cells are neural stem cells and the disorder is a neurological disorder of the peripheral nervous system.

In addition, the immortalized cell line may be used to screen drugs which may effect the development, differentiation and/or function of the cells. These include both small molecule organic pharmaceuticals as well as growth factors.

Disimmortalized cells are particularly useful in transplant or implant applications, since the immortalizing oncogenes are removed prior to introduction into the body, thus eliminating the potential creation of tumors as a result of the immortalizing gene. The methods of the invention are applicable to both human therapy and veterinary applications, for example for the human use of non-human cells. Thus the methods and constructs of the invention may be used with cells from such animals as humans, pigs, primates, rodents such as mice and rats, dogs, cows and sheep.

The following is presented by way of example and is not to be construed as a limitation on the scope of the invention. Further, all references referred to herein are expressly incorporated by reference.

EXAMPLE

In this example, a standard moloney murine leukemia virus retroviral vector was used and modified. A standard recombinant replication incompetent retroviral vector harboring the v-myc oncogene was modified so as to place loxP sites flanking the v-myc coding sequence and so as to place a βgalactosidase coding sequence downstream (3') to the IoxP-v-myc-loxP sequences. These modifications were accomplished by standard molecular biological procedures familiar to those skilled in the art and involving restriction enzyme, digestion, ligation, PCR amplification, bacterial transformation, plasmid isolation and further characterization and sequencing.

To confirm that this modified recombinant retroviral construct was in fact capable of producing recombinant infectious viral particles, the following experiments were first performed. To produce infectious replication incompetent virus particles, the construct was transfected into the packaging line BOSC 23. Following transient transfection of the BOSC 23 cells, three days later supernatants from these transfected cells were collected containing the retroviral particles. The tiler of infectious virus in these supernatants was between 105 and $10^6$ pfu/ml. These viral supernatants were then used to infect NIH 3T3 cells. Staining of these cells several days post infection with an antibody to avian v-myc confirmed that many of these cells expressed the v-myc oncogene. Fixation and staining of sister cultures with the Xgal reagent confirmed, that as predicted from the design of the vector, none of the infected cells expressed βgalactosidase. This experiment therefore revealed two important things: 1) that the construct was capable of being packaged into infectious retrovirus and 2) that the v-myc oncogene coding sequences contained in that vector could be transcribed and translated into protein in infected cells.

Transfection of the cre enzyme into these retrovirally infected cells resulted in excision of the v-myc coding sequences and concomitant activation of βgalactosidase enzyme activity. This was accomplished by transfecting the retrovirally infected cells with an expression construct in which the cre recombinase was under the control of the cytomegalovirus CMV enhancer. Twenty-four to forty-eight hours after their transfection the cells were fixed and processed for Xgal staining. This staining revealed that many of the retrovirally infected cells now showed βgalactosidase enzyme activity evidenced by the blue reaction product in their nuclei. No βgalactosidase activity was observed in control cultures transfected with the same CMV expression vector lacking the cre coding sequences. Staining of the cre transfected cells with antibody to the v-myc oncogene confirmed that these transfected cells no longer expressed the v-myc oncogene, as expected based on its excision from the provirus by the cre recombinase.

These experiments thus indicate that the cre recombinase is able to excise the v-myc oncogene sequence from an integrated provirus in a mammalian cells genome and that this excision of the oncogene results in concomitant activation of the downstream reporter gene, in this case βgalactosidase, as expected based on the design of this vector.

The expression of the v-myc oncogene from this retroviral construct produced functional v-myc sequences that were capable of immortalizing a primary cell type. This was done using primary mouse embryo fibroblasts. The fibroblasts were isolated and cultured by standard procedures and then infected with the retroviral vector encoding the modified v-myc oncogene flanked by the loxP sequences containing the βgalactosidase marker gene downstream. This vector referred to as retmycgal. The infected cells were placed under selection by culturing them in the presence of 6 mM histidine. The retroviral vector also contains the histidinol dehydrogenase gene. Therefore, cells expressing the integrated provirus will survive in the presence of 6 mM histidine whereas uninfected cells will die. A control plate of uninfected cells was carried in the absence of 6 mM histidine for a comparison of the growth rates between uninfected and infected cells. After four to five weeks of growth in culture involving approximately six passages, a clear difference was visible between the histidine resistant myc infected cells and the uninfected cells. The uninfected control fibroblast by this time had reached senescence and had flattened out and stopped dividing. By contrast, cells infected with the retmycgal retroviral construct continued to exhibit robust proliferation in culture. Fixation and staining of some of these cells with antibody to v-myc revealed abundant expression of the avian v-myc oncogene in the nuclei of these infected fibroblasts, confirming that their immortalized state was due to the expression of the v-myc oncogene. As expected, no βgalactosidase activity was detected in the cells.

The myc coding sequences could be excised from the genome of the established infected cells by transfection of a cre expression construct into the cells. This excision of myc resulted in concomitant activation of the βgalactosidase gene, as we had shown previously in the case of the transiently infected cells. Following transfection of the CMV cre construct into these cells, many blue cells were detectable by Xgal staining. These data therefore demonstrate that the cre recombinase is able to excise the v-myc coding sequences and activate expression of the downstream marker 13galactosidase even in stably infected primary cells that have been passaged at least six times. More importantly, they indicate that expression of the v-myc coding sequences from the integrated provirus is in fact capable of functionally immortalizing these primary mouse fibroblasts as expected.

In summary, this example demonstrates using primary mouse embryo fibroblasts, that is possible to immortalize primary cells by infecting them with the retmycgal retroviral vector to stably passage these immortalized cells for at least six generations and then to disimmortalize the cells by excising the oncogene myc sequences from their genome by transfection of these cells with acre expression construct.

---

---

What is claimed is:

1. An immortalized mammalian cell that contains in the genome of said cell exogenous nucleic acid comprising at least a first and a second recombinase target site flanking an immortalization gene, wherein said first and second target sites mediate excision of said immortalization gene when said first and second target sites are contacted with a recombinase.

2. An immortalized cell line according to claim 1 wherein said exogeneous nucleic acid further comprises a selection marker gene.

3. An immortalized cell line according to claim 2 wherein said selection marker gene is a negative selection marker gene.

4. An immortalized cell line according to claim 2 wherein said nucleic acid further comprises a STOP site.

5. An immortalized cell line according to claim 1 wherein said exogeneous nucleic acid further comprises a first selection marker gene and a second selection marker gene.

6. An immortalized cell line according to claim 5 wherein said second selection marker gene is not between the first and second recombinase target sites.

7. A method for creating an immortalized cell that contains recombinase target sites flanking an immortalization gene in the genome of said immortalized cell, said method comprising transforming a cell with exogeneous nucleic acid comprising a) a first recombinase site;
b) an immortalization gene; and c) a second recombinase site;

such that in the absence of a recombinase said exogenous nucleic acid is incorporated into the genome of said cell.

8. A method according to claim 7 wherein said nucleic acid further comprises at least one selection marker gene.

9. A method according to claim 8 wherein said selection marker gene is a negative selection marker.

10. A method for the disimmortalization of an immortalized cell that contains exogenous nucleic acid comprising recombinase target sites flanking an immortalization gene in the genome of said immortalized cell, said method comprising contacting said recombinase target sites with a recombinase which recognizes said recombinase target sites, wherein said recombinase is produced by expression of a recombinase nucleic acid within said cell.

11. A method according to claim 10 wherein said expression is achieved by transforming said immortalized cell with a recombinase nucleic acid encoding said recombinase and maintaining said transformed cells under conditions where said recombinase is expressed and said immortalization gene is excised.

12. A method for the disimmortalization of an immortalized cell comprising:
   a) incorporating exogeneous nucleic acid comprising:
      i) a first recombinase target site;
      ii) an immortalization gene;
      iii) a negative selection marker gene; and
      iv) a second recombinase target site;
      into the genome of a cell to produce an immortalized cell which contains an excisable immortalization gene in an orientation such that excision of the sequence between the recombinase target sites excises the immortalization gene and the negative selection marker; and
   b) contacting said recombinase target sites with a recombinase which recognizes said recombinase target sites such that said immortalization gene and said negative selection marker gene are excised, wherein said recombinase is produced by expression of a recombinase gene within said cell.

13. A method according to claim 12 wherein said expression is achieved by transforming said immortalized cells with a vector encoding a recombinase which recognizes said recombinase target sites under conditions wherein said recombinase is expressed.

14. A method according to claim 12 wherein said exogeneous nucleic acid further comprises a gene for a recombinase that recognizes said recombinase target sites, wherein said recombinase gene is operably linked to an inducible promoter, and said expression is achieved by growing said immortalized cells under conditions wherein said recombinase is expressed.

15. A method according to claim 12 wherein said exogeneous nucleic acid further comprises a gene for a recombinase that recognizes said recombinase target sites, wherein said recombinase gene is operably linked to an inducible promoter, and said contacting is achieved by growing said immortalized cells under conditions wherein said recombinase is expressed.

16. A method according to claim 12 wherein said method further comprises selecting for disimmortalized cells in the presence of a negative selection agent.

17. A method according to claim 12 wherein said exogeneous nucleic acid further comprises a positive selection gene.

18. A method for the disimmortalization of an immortalized cell comprising:
   a) incorporating exogeneous nucleic acid comprising:
      i) a first recombinase target site;
      ii) an immortalization gene;
      iii) a selection marker gene; and
      iv) a second recombinase target site;
      into the genome of a cell to produce an immortalized cell which contains an excisable immortalization gene in an orientation such that excision of the sequence between the recombinase target sites excises the immortalization gene, resulting in the expression of the selection marker; and
   b) contacting said recombinase target sites with a recombinase which recognizes said recombinase target sites such that said immortalization gene is excised, wherein said recombinase is produced by expression of a recombinase gene within said cell.

19. A method according to claim 18 wherein said nucleic acid further comprises a STOP site.

20. A method according to claim 17 wherein said expression is achieved by transforming said immortalized cells with a vector encoding a recombinase which recognizes said recombinase target sites under conditions wherein said recombinase is expressed.

21. A method according to claim 17 wherein said exogeneous nucleic acid further comprises a gene for a recombinase that recognizes said recombinase target sites operably linked to an inducible promoter, and said expression is achieved by growing said immortalized cells under conditions wherein said recombinase is expressed.

22. A method according to claim 18 wherein said method further comprises selecting for disimmortalized cells that express said selection marker gene.

23. A method for the disimmortalization of an immortalized cell comprising:
   a) incorporating exogeneous nucleic acid comprising:
      i) a first recombinase target site;
      ii) an immortalization gene;
      iii) a first selection marker gene;
      iv) a second recombinase target site; and
      v) a second selection marker gene;
      into the genome of a cell to produce an immortalized cell which contains an excisable immortalization gene in an orientation such that when the immortalization gene is expressed, the first selection marker gene is also expressed and the second selection marker gene is not expressed and when said immortalization gene is excised said second selection marker is expressed; and
   b) contacting said recombinase target sites with a recombinase which recognizes said recombinase target sites such that said immortalization gene is excised, wherein said recombinase is produced by expression of a recombinase gene within said cell.

24. A method according to claim 23 wherein said expression is by transforming said immortalized cells with a vector encoding a recombinase which recognizes said recombinase target sites under conditions wherein said recombinase is expressed.

25. A method according to claim 23 wherein said exogeneous nucleic acid further comprises a gene for a recombinase that recognizes said recombinase target sites, wherein said recombinase gene is operably linked to an inducible promoter, and said expression is by growing said immortalized cells under conditions wherein said recombinase is expressed.

26. A method according to claim 23 wherein said nucleic acid further comprises an additional exogeneous gene.

27. A method according to claim 23 wherein said nucleic acid further comprises a STOP site.

28. A cell according to claim 1 wherein said recombinase is Cre recombinase.

29. A method according to claim 7 wherein said recombinase is Cre recombinase.

30. A method according to claim 10 wherein said recombinase is Cre recombinase.

31. A method according to claim 12 wherein said recombinase is Cre recombinase.

32. A method according to claim 18 wherein said recombinase is Cre recombinase.

33. A method according to claim 23 wherein said recombinase is Cre recombinase.

34. A cell according to claim 1 wherein said recombinase is FLP recombinase.

35. A method according to claim 7 wherein said recombinase is FLP recombinase.

36. A method according to claim 10 wherein said recombinase is FLP recombinase.

37. A method according to claim 12 wherein said recombinase is FLP recombinase.

38. A method according to claim 18 wherein said recombinase is FLP recombinase.

39. A method according to claim 23 wherein said recombinase is FLP recombinase.

* * * * *